(12) United States Patent
Grottel et al.

(10) Patent No.: US 7,924,852 B2
(45) Date of Patent: Apr. 12, 2011

(54) METHOD AND NETWORK FOR TRANSFERRING DATA AND SIGNALS

(75) Inventors: Joachim Grottel, Lauf (DE); Harald Karl, Fürth (DE); Friedrich Lindner, Erlangen (DE); Andreas Tröltzsch, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 573 days.

(21) Appl. No.: 11/817,050

(22) PCT Filed: Feb. 22, 2006

(86) PCT No.: PCT/EP2006/060168
§ 371 (c)(1),
(2), (4) Date: Aug. 24, 2007

(87) PCT Pub. No.: WO2006/089903
PCT Pub. Date: Aug. 31, 2006

(65) Prior Publication Data
US 2008/0259935 A1  Oct. 23, 2008

(30) Foreign Application Priority Data
Feb. 24, 2005  (DE) .................... 10 2005 008 503

(51) Int. Cl.
*H04L 12/28* (2006.01)
*H04L 12/56* (2006.01)
(52) U.S. Cl. .................... 370/396; 370/216; 370/248

(58) Field of Classification Search .................. 370/396, 370/394
See application file for complete search history.

(56) References Cited

U.S. PATENT DOCUMENTS

| 5,220,563 | A | 6/1993 | Grenot et al. |
| 5,566,170 | A * | 10/1996 | Bakke et al. ............... 370/392 |
| 6,263,393 | B1 * | 7/2001 | Funaya et al. ............. 710/316 |
| 6,331,981 | B1 | 12/2001 | Harth et al. |
| 6,600,746 | B1 | 7/2003 | Petersen |
| 6,636,514 | B1 | 10/2003 | Caves |
| 6,795,436 | B1 * | 9/2004 | De Vriendt et al. ......... 370/395.1 |
| 2004/0028408 | A1 * | 2/2004 | Cox et al. .................... 398/66 |

OTHER PUBLICATIONS

SONET Telecommunications Standard Primer, Tektronix, Inc. copyright 2001, 35 pages.*
ATM-Netzwerke: Aufbau-Funktion-Performance (1993), pp. 112-118.

* cited by examiner

*Primary Examiner* — Daniel Wu
*Assistant Examiner* — Frederick Ott
(74) *Attorney, Agent, or Firm* — Schiff Hardin LLP

(57) ABSTRACT

In a method and network for transferring data and signals between terminal equipment via one or more switching stations, the data and digitized signals are combined in cells, with each cell having a header in which connection information is contained that designates a transmission or routing target. The terminal equipment and switching stations are synchronized so that the cells are transferred in a synchronized manner via one or more switching stations. Signals and high quality of service (QoS) data thus can be transferred through the same network.

15 Claims, 7 Drawing Sheets

| $DCI_9$ | $DCI_8$ | $DCI_7$ | $DCI_6$ | $DCI_5$ | $DCI_4$ | $DCI_3$ | $DCI_2$ |
|---|---|---|---|---|---|---|---|
| $DCI_1$ | $DCI_0$ | $EED_1$ | $EED_0$ | $FPI_2$ | $FPI_1$ | $FPI_0$ | $PV$ |
| $S1_7$ ($S39$) | $S1_6$ | $S1_5$ | $S1_4$ | $S1_3$ | $S1_2$ | $S1_1$ | $S1_0$ |
| $S2_7$ | $S2_6$ | $S2_5$ | $S2_4$ | $S2_3$ | $S2_2$ | $S2_1$ | $S2_0$ |
| $S3_7$ | $S3_6$ | $S3_5$ | $S3_4$ | $S3_3$ | $S3_2$ | $S3_1$ | $S3_0$ |
| $S4_7$ | $S4_6$ | $S4_5$ | $S4_4$ | $S4_3$ | $S4_2$ | $S4_1$ | $S4_0$ |
| $S5_7$ | $S5_6$ | $S5_5$ | $S5_4$ | $S5_3$ | $S5_2$ | $S5_1$ | $S5_0$ ($S0$) |
| $D1_7$ ($D31$) | $D1_6$ | $D1_5$ | $D1_4$ | $D1_3$ | $D1_2$ | $D1_1$ | $D1_0$ |
| $D2_7$ | $D2_6$ | $D2_5$ | $D2_4$ | $D2_3$ | $D2_2$ | $D2_1$ | $D2_0$ |
| $D3_7$ | $D3_6$ | $D3_5$ | $D3_4$ | $D3_3$ | $D3_2$ | $D3_1$ | $D3_0$ |
| $D4_7$ | $D4_6$ | $D4_5$ | $D4_4$ | $D4_3$ | $D4_2$ | $D4_1$ | $D4_0$ ($D0$) |
| $CC_7$ | $CC_6$ | $CC_5$ | $CC_4$ | $CC_3$ | $CC_2$ | $CC_1$ | $CC_0$ |

FIG 4

| $DCI_9$ | $DCI_8$ | $DCI_7$ | $DCI_6$ | $DCI_5$ | $DCI_4$ | $DCI_3$ | $DCI_2$ |
|---|---|---|---|---|---|---|---|
| $DCI_1$ | $DCI_0$ | $EED_1$ | $EED_0$ | $FPI_2$ | $FPI_1$ | $FPI_0$ | $PV$ |
| $S1_7$ ($S39$) | $S1_6$ | $S1_5$ | $S1_4$ | $S1_3$ | $S1_2$ | $S1_1$ | $S1_0$ |
| $S2_7$ | $S2_6$ | $S2_5$ | $S2_4$ | $S2_3$ | $S2_2$ | $S2_1$ | $S2_0$ |
| $S3_7$ | $S3_6$ | $S3_5$ | $S3_4$ | $S3_3$ | $S3_2$ | $S3_1$ | $S3_0$ |
| $S4_7$ | $S4_6$ | $S4_5$ | $S4_4$ | $S4_3$ | $S4_2$ | $S4_1$ | $S4_0$ |
| $S5_7$ | $S5_6$ | $S5_5$ | $S5_4$ | $S5_3$ | $S5_2$ | $S5_1$ | $S5_0$ ($S0$) |
| $D1_7$ ($D31$) | $D1_6$ | $D1_5$ | $D1_4$ | $D1_3$ | $D1_2$ | $D1_1$ | $D1_0$ |
| $D2_7$ | $D2_6$ | $D2_5$ | $D2_4$ | $D2_3$ | $D2_2$ | $D2_1$ | $D2_0$ |
| $D3_7$ | $D3_6$ | $D3_5$ | $D3_4$ | $D3_3$ | $D3_2$ | $D3_1$ | $D3_0$ |
| $D4_7$ | $D4_6$ | $D4_5$ | $D4_4$ | $D4_3$ | $D4_2$ | $D4_1$ | $D4_0$ ($D0$) |
| $CC_7$ | $CC_6$ | $CC_5$ | $CC_4$ | $CC_3$ | $CC_2$ | $CC_1$ | $CC_0$ |

METHOD AND NETWORK FOR TRANSFERRING DATA AND SIGNALS

BACKGROUND OF THE INVENTION

1. Field of the Invention

The present invention concerns a method for data and signal transmission between terminal equipment via one or more switching stations in a distributed system. The invention also concerns a network fashioned for data and signal transmission according to such a method.

2. Description of the Prior Art

Medical-technical systems, in particular modern CT systems, have a number of connection lines between the individual sub-units, via which lines control signals for the activation of components of the system and digital data such as, for example, measurement data are transferred. Due to continuous development, CT systems require a flexible and scalable architecture that should strive to achieve a high reliability and a simple implementation of service tasks while also minimizing the cost expenditure for expansions.

Like the architecture of other medical-technical systems (for example in the field of magnetic resonance tomography), the architecture of currently used CT systems is based on the usage of a standard control network such as, for example, CAN (Controller Area Network) for the transmission of digital data with low speed. Furthermore, additional connection lines are used via which (normally logic) signals (such as, for example, control signals) are respectively transferred on the basis of a separate protocol and a separate specification, which signals must be updated frequently and very quickly during the system operation. This results in a number of connections with respectively different protocols, which makes a future improvement and expansion of such a system difficult.

A comparable problem also exists in other technical fields in which both hardware signals and data must be transferred, wherein a high quality of service (also designated as QoS (Quality of Service: measure for the reliability of the adherence to real time) in the following) must be achieved for a portion of the data or signals.

The previously used transmission technologies provide separate transmission of real hardware signals via hardware lines and data via field buses such as CAN or Profinet. Transmission technologies such as ATM (Asynchronous Transfer Mode), Sonet (Synchronous Optical Network) or Realtime Ethernet are known for the data transfer.

DE 691 16 538 T2 discloses a device for transmission of signaling data in an asynchronous network, in particular an ATM network, in order to be able to exchange data between synchronous and asynchronous networks. In the method of this publication the signaling data of the different channels from the synchronous network are detected and examined for state changes. Given each detected state change, an ATM cell is generated that comprises includes the appertaining channel number in its header and the new signaling is designated in the usage information field. This cell is then sent in the ATM network. In this manner data are transferred between terminal equipment lying outside of the ATM network via switching stations of the ATM network.

SUMMARY OF THE INVENTION

The object of the present invention is to specify a method as well as a network for data and signal transfer with which the communication of both real hardware signals and of data via the same network is possible with a high QoS.

This object is achieved in accordance with the invention by a method for data and signal transmission between terminal equipment (devices) via one or more switching stations (switches) in a distributed system, wherein data and digitized signals to be transmitted are merged into cells that each include a header region (header) containing connection information about at least one transmission or relay target of the data in the respective cell. The cells, which aside from the header each have at least one block for the data and at least one block for the digitized signals, are transferred synchronously via the one or more switching stations.

In the invention method the transmission of information (i.e. of the data and signals) thus ensues as in power-switching networks, but the switching in the switching stations ensues as in packet-switching networks. This enables an independent transfer of data and digitized signals in the individual cells, which can additionally be selected short enough in order to ensure a high updating rate of the signals. Moreover, a high QoS, as is required for the transmission of hardware signals, is achieved by the simultaneous synchronous transmission of the cells.

The method enables the transmission both of real hardware signals and of data over a real network. This network can be used independently for data or signal transmission as well as for the combined transmission of hardware signals and data. The proportions of data and signals can be predetermined in arbitrary ratios. The method is suitable for all applications in which data and/or signals must be transferred via a network under hard realtime requirements (<100 μs). Uniform interfaces both for signals and for data are provided in the respective system due to the use of the present method. Synergies can be utilized in this manner and the development costs are thereby reduced. The reliability of the system is increased and the unit costs for the production of the system components are reduced by the reduction of the number of plug components that is achieved as a result.

The network according to the invention for data and signal transmission has, in a known manner, a number of terminal equipment units that can communicate with one another via wired and/or wireless connections via one or more switching stations. The terminal equipment and switching stations each are formed by modules that are fashioned for the synchronization, the generation of cells and the reception and dispatching of cells according to the method described above.

In the present method the digitized signals are advantageously incorporated into the cells independently of the connection information for the data. This enables the transmission of digitized signals with every dispatched cell, independently of the terminal equipment unit or the terminal equipment units for which the data in the cell are destined. In the switching station the digitized signals in the respective cell are then relayed, for example corresponding to a register entry in the switching station that includes the relay targets for individual bit or byte positions in the block provided for the digitized signals within each cell. For this purpose, new cells are generated to which the read, digitized signals are newly distributed corresponding to their forwarding target. A signal received at one port of the switching station can thus be sent to arbitrary output ports. The register within the switching stations can hereby advantageously be freely configured. This can ensue via the network, such that a programming of the switching stations is possible during the operation.

The transfer of the cells advantageously ensues in periodically recurring frames each having the same number of cells. Information about the position of this cell within the frame is incorporated into the header of each cell.

In an embodiment of the present method, fill characters are inserted between the cells within a frame upon transmission. During the transmission operation the terminal equipment or switching stations respectively detect any deviation of the transmission points in time from a global transmission point in time (predetermined via the synchronization) and correct this deviation by altering the length of individual fill characters between the cells. Cell losses in the transmission that could occur due to local clock frequencies of the individual components of the network that deviate slightly from one another can be prevented in this manner.

Since in many cases the length of a cell is not sufficient for the transmission of a number of complete signals, the bits of the values of one or more digitized signals are advantageously distributed among multiple cells within the frame. Given sufficient cell length a single, signal can either be transferred with each cell and thus be updated, or can be distributed among a number of (for example n) successive cells, in particular given a number of signals to be transferred, such that in this case an updating ensues after every n-th cell.

Since, in the present method, the delay between the receipt of a cell and the dispatching of the new cell(s) based thereupon is constant and known (or can be determined in advance) within each component of the network, just like the delay of the cells between the different network components, the transmission points in time of the cells in the individual components can be controlled such that the respective newly generated cells can be dispatched immediately after their generation, i.e. without greater delay. The transmission time thus is optimized in this manner, and the QoS is achieved due to the precise predictability of the transmission time and the residence time of the individual data and signals in the network components.

For connections for data and/or signal transmission between terminal equipment for which a high QoS is required, one or more time slices of a periodically recurring sub-frame (which sub-frame includes a fixed number of time slices) are reserved for the transmission. A sub-frame has a number of individual frames. In the present method the time slices are likewise synchronized. Furthermore, the possibility exists to newly determine the time slices in the switching stations using the additional connection information of the respective cell. Data regarding an established time slice can be sent to arbitrary output ports via a switching station. The connection identifier (i.e. the connection information) of the respective cell thus can be changed in the switching station.

The cells advantageously include an error code dependent on the cell content, using which error code the reception of inaccurate cells is detected in the switching station or the terminal equipment. Given detection of an incorrect cell, the values of the digitized signals that were transferred entirely or in part with this cell are discarded. This can ensue, for example, by setting the signal values to zero. Given transmission errors or upon failure of cells the signals pertaining to these are thus immediately discarded or erased, and all other signals not pertaining to these remain in their current state. In the present method this mechanism can also be activated or deactivated. In the switching station an error signal can additionally, advantageously be set in all outgoing cells that relay signals of the discarded cells.

BRIEF DESCRIPTION OF THE DRAWINGS

FIG. 4 shows an example for the design of a cell in the present method.

DESCRIPTION OF THE PREFERRED EMBODIMENT

The method explained in the following example according to the present invention defines a transmission protocol on layer 1 and layer 2 of the ISO-OSI reference model. The length of the individual cells as well as their arrangement can naturally also be selected differently from the example dependent on the respective application.

The entire system (composed of the transmission protocol and the network components) is also designated as SiDaNet (Signal Data Network) in the following. This system enables the combined transport of binary signals, variables up to 32 bits in length, and data packets as well as the remote access to memory regions in the network components via the same network. All different information types can be transferred over the network with full QoS. The same network can therewith be used both for the signal transfer with high real-time requirements and for the simple data transfer.

At least two different types of network components exist in the network. Terminal equipment (also called a device) generate and consume data traffic. The term "data traffic" encompasses the entire content of cells, i.e. also digitized signals. Each terminal equipment unit has precisely one port and does not relay incoming data traffic. Switching stations (also called switches) mediate the data traffic. The mediation of the data traffic from a reception port to one or more transmission ports can be dynamically configured during the operation of the network. Switching stations have at least two ports. In addition to these two component types of the present network, one or more routers can also optionally be provided that transfer the data traffic into one or more other networks or inject the data traffic from these into the existing network. Other networks can, for example, be the Ethernet or another SiDaNet.

Figure 1:
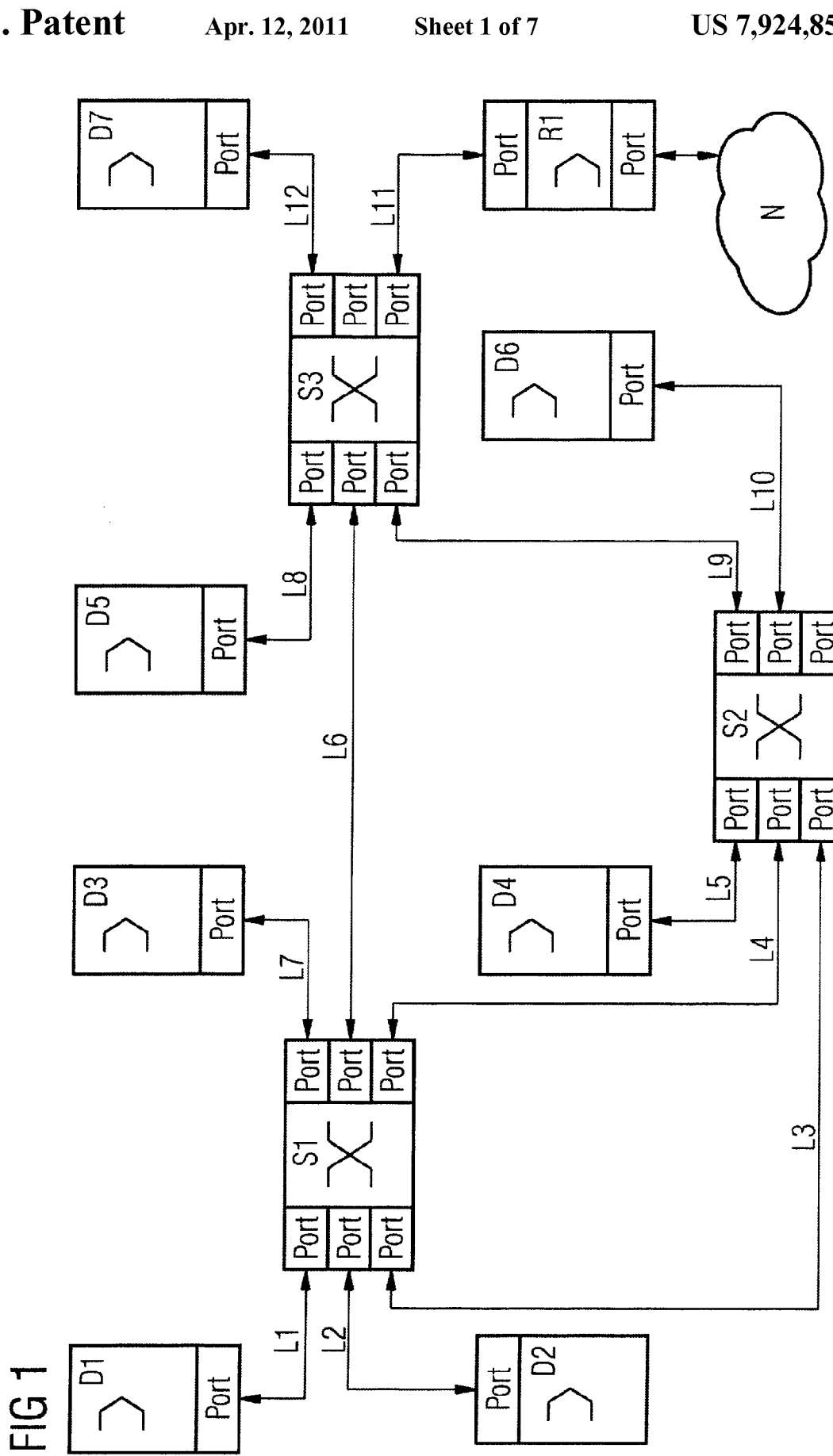
FIG. 1 shows an example for the design of a network for implementation of the present method.

FIG. 1 schematically shows an example for the design of a network with 7 terminal equipment D1-D7 that are connected with one another via 3 switching stations S1-S3. The individual links are designated with L1-L12. The links can be realized wirelessly or, for example, via wire or fiber connections. A router R1 that establishes the connection to another network N is also shown in FIG. 1. In the present example each link establishes a bidirectional full-duplex connection between exactly two ports of the network.

The administration of the data traffic ensues based on the connection, meaning that data are only transported between two terminal equipment units after a connection is established between the two terminal equipment units. All information types (also encompassing digitized signals) are transported in cells that exhibit a constant number of bytes for data, digitized signals and the connection information. This enables the transport of multiple connections over a single link. The switching station uses the connection information in each cell in connection with information in a local register or memory in order to determine the transmission ports and QoS requirements for the data and signals in a received cell.

In the present example digitized signals, variables and packets can be transported with the method and memory regions can be accessed. In each cell, signals are contained independent of the connection for which the cell is used. In each switching station each received signal bit of each port can be connected with each bit of one or more output ports. However, this possibility is advantageously limited to signal groups. Each signal bit is associated with a signal group, but only the signal bits within a signal group can be intermixed in a switching station. The total number of the signal bits and their association with signal groups are established in a signal profile.

In the present example variables have a fixed information length of 4 bytes that always belong together. Exactly one variable can be transferred in a cell. The interpretation of the variable ensues via the connection information with which the variable is transferred between the terminal equipment.

Packets represent a data type that requires no QoS or only a weak QoS, but include a number of bytes. The length of a data packet can vary between 1 and 2044 bytes, such that this cannot be transported in a single cell. Packets are therefore divided among multiple cells and recombined at the target apparatus.

The present network also enables remote accesses (read and write accesses) from an end apparatus to the memory of another end apparatus or a switching station. The connection then specifies the target apparatus and the memory region in the event that more than one memory region exists in the target apparatus. Data must be transferred in both directions for the memory access, such that this data type is only possible between exactly two network components. The maximum address range amounts to 64 kwords of respectively 16 bits. Each access process to a memory in one direction is transferred in a cell.

The design of the components of the network is described in the following with regard to the different layers of the ISO reference layer model. The data link layer represents the layer 2 of this model. In addition to the components of FIGS. 2 and 3, each switching station or and each terminal equipment unit also exhibits an administration interface via which the configuration and monitoring of the state of the individual component modules ensues. This administration interface is not explicitly shown in FIGS. 2 and 3.

Figure 2:
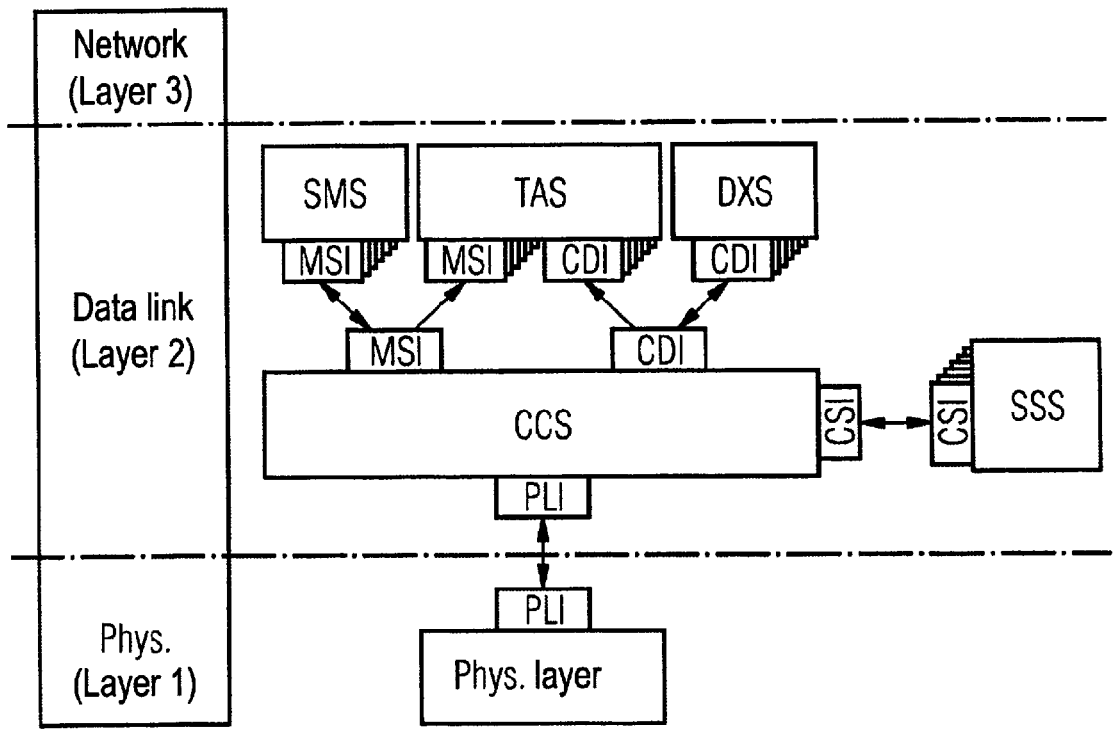
FIG. 2 shows an example for the design of a switching station in the present network.

FIG. 2 schematically shows the design of a switching station in relation to the top layers. The data link layer of a switching station comprises a signal multiplexer module (SMS: Signal multiplexing Sub-layer), a data switching module (DXS: Data Switching Sub-layer), a traffic analysis module (TAS: Traffic Analysis Sub-layer), a cell processing module (CCS: Cell Conditioning Sub-layer) as well as a switch synchronization module (SSS: Switch Synchronization Sub-layer). Interfaces between these modules are additionally provided, of which the multiplexer signal interface (MSI: Multiplex Signal Interface), the cell data interface (CDI: Cell Data Interface), the interface to the physical layer (PLI: Physical Layer Interface) and the cell synchronization interface (CSI: Cell Synchronization Interface) are shown. The signal multiplexer module as well as the data switching module are present multiple times in a switching station, once for each port.

The cell processing module primarily has the task different information elements of a cell in the transmission direction and to extract the different information from the cell in the reception direction. Furthermore, this module checks the integrity of the cell via the error code (cell redundancy code) and controls the start point in time of the transfer of a cell in order to ensure the synchronous operation of the entire network.

The task of the switch synchronization module SSS is the synchronization of all ports of the switching station. The SSS can operate in two operating modes, as master or as repeater. As master it provides the global clock reference for the entire SiDaNet; in the repeater operating mode it synchronizes the switching station and all network components with the global clock reference that is received from the master or from another repeater at an input port.

The signal multiplexer module distributes the signals of each cell to the target ports. The distribution rules for each signal bit of a port are established via the administration interface. The data switching module distributes the data potion of each cell to the corresponding target port or ports. The distribution rules for each connection of a port are likewise established via the administration interface. The traffic analysis module serves for the analysis and the recording of the outgoing and incoming traffic.

Figure 3:
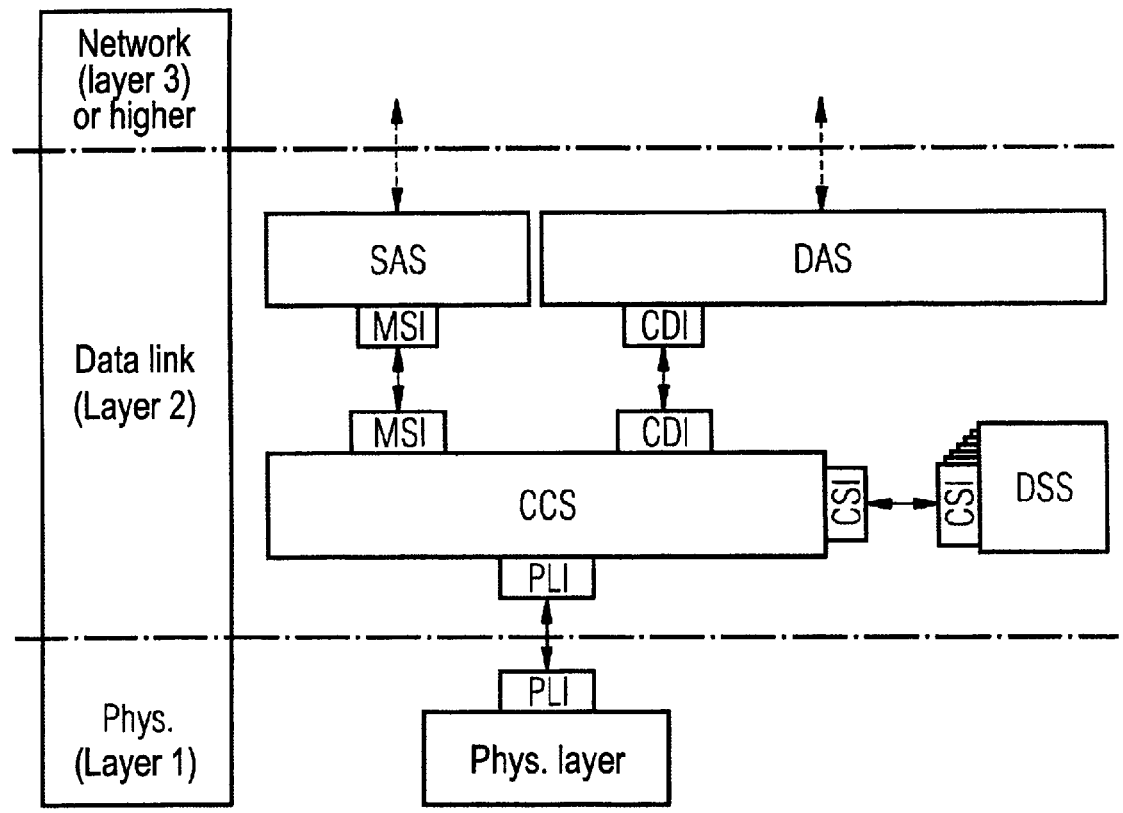
FIG. 3 shows an example for the design of an end apparatus in the present network.

FIG. 3 shows an example for the design of a terminal equipment unit in the present network. In FIG. 3 the access to the higher layers is only indicated by the unbroken arrows and is not remarked upon in detail since this is not a component of the present invention.

The terminal equipment design shown in FIG. 3, includes at least the following modules. The device synchronization module (DSS: Device Synchronization Sub-layer) implements the synchronization of the transmission time with the reception time in order to attain an identical data rate in both directions. The DSS always operates as slave and is synchronized via the SSS of the switching station to the opposite side of the link. The signal access module (SAS: Signal Access Sub-layer) controls the access of the hardware and application software of the end apparatus to the signals. The data access module (DAS: Data Access Sub-layer) controls the access of the hardware and application software of the end apparatus to the different data types: variables, memory and packets. The cell processing module (CSS) as well as the interfaces shown in FIG. 3 are identical to those of FIG. 2 and have already been explained in this context.

The administration interface provided in both network components enables the control and diagnosis of the data link layer (DLL: Data Link Layer) independently of data traffic. The interface comprises a register set with individual read and/or write access. The access ensues fully synchronously with the system clock (SysClk).

In the present system the signals and data are transferred in individual cells. FIG. 4 shows an example for the design of such a cell. The cell comprises a header (2 bytes), a block for the signals (5 bytes), a block for the data (4 bytes) and an end region (1 byte). In the present system all signals or signal profiles and data types are transported with the identical cell structure. The header includes, among other things, the connection information DCI (Data Connection Identifier) on the basis of which the cell is transported between the terminal equipment via the network and the frame position indicator (FPI: Frame Position Indicator). This indicates whether the cell is the first, second etc. within a frame. These two elements of the header of the cell are analyzed in a switching station in order to implement the correct switching. The end-to-end delimiter EEB (End-to-End Delimiter) is not interpreted in the switching station. It is used in order to provide higher control functions for the data types "memory" and "packet". The protocol version PV (Protocol Version) enables further protocol expansions.

The signal block contains 5 signal bytes Sn that are transported independently of the connection information of the cell. Since 5 bytes only enable the transfer of 40 bits with one cell, some bytes within a frame can be multiplexed in order to increase the total number of the signal bits. The multiplex scheme is part of the signal profile, which is discussed in detail below.

The data block includes 4 bytes of data Dn that transport the information for the data types "variable", "memory" and "packet". The interpretation of the received data at the target apparatus ensues via the connection information that is encoded in the DCI field in the header of the cell. The end region contains 1 byte with the error code CC. This is calculated over all preceding 11 bytes of the cell.

Figure 5:
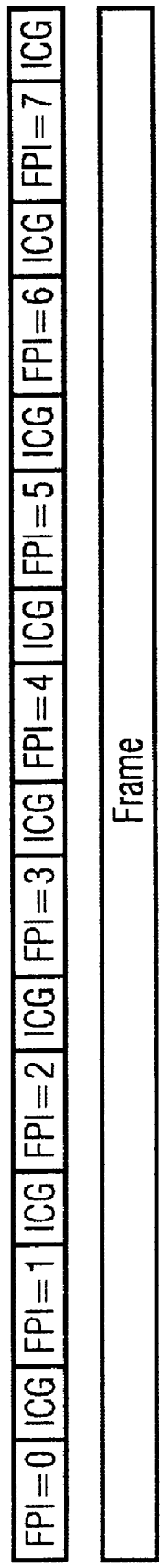
FIG. 5 shows an example for the design of a frame in the present method.

For the transmission of more than 40 signal bits in connection with the QoS requirements and the synchronous operation of the network it is necessary to define an additional structure above the cell: the frame. 8 cells at a time are combined into a frame, and each cell is spaced from the following cell by a fill character ICG (Inter-Cell Gap). FIG. 5 shows the design of such a frame, whereby the individual cells are provided with the frame position indicator FPI. A new frame starts with the first cell, which is characterized by an FPI of 0. The ICGs are used to synchronize transferred bytes with received bytes in order to compensate for a possible difference between local reception and transmission oscillator frequencies of the appertaining network components. For this purpose, the length of the ICG can be increased or reduced. The length of this ICG varies dependent on whether the respective component provides the global clock reference for the entire network (sync master) or is synchronized from the network (sync slave or sync repeater). The length of the ICG is a multiple of a byte. A sync master generates ICGs of an always-constant length of 2 bytes. A sync slave or a sync repeater produces ICGs with a length of 1, 2 or 3 bytes, respectively dependent on the currently necessary correction of the oscillator frequencies.

In the following the signal transport in the network is discussed in detail. Each cell can transport 40 signal bits in parallel. Since more than 40 signal bits are normally required for each port, the signal bits are structured in signal groups. The number of different signal groups, the number of bits within each group and the transfer rate of each group represent a signal profile. A signal profile is constant for the entire network and has the following design: SPnn:m-nn:m-...nn:, wherein nn indicates the number of the bits within the signal group and m indicates the multiplex ratio (for which the values of 1, 2, 4 and 8 are allowed). The value of 1 means that the signals of this signal groups are transferred within each cell. The signal is transferred in every second cell given a value of 2, in every fourth cell given a value of 4 and in every eighth cell given a value of 8.

Figure 6:
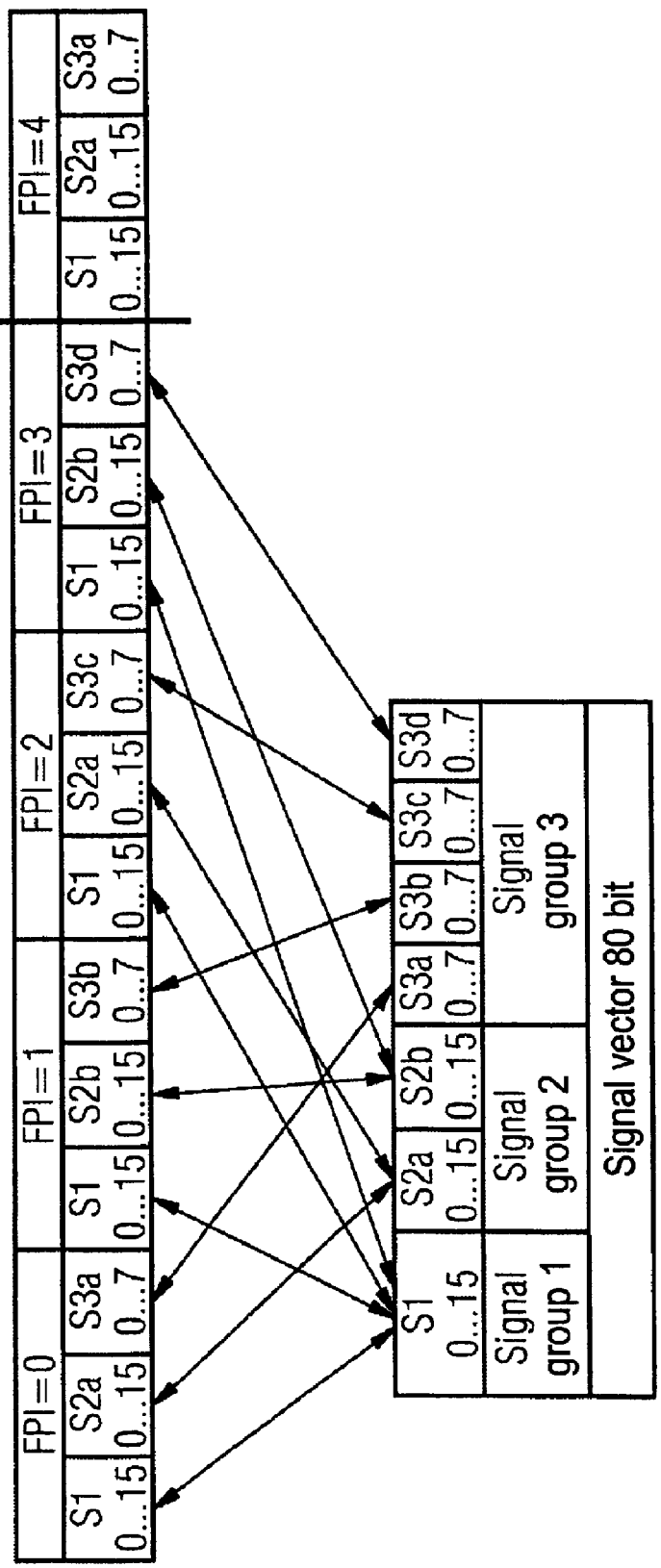
FIG. 6 shows an example for the division of digitized signals into a plurality of cells within a frame.

A standard profile for the present SiDaNet is SP16:1-32: 2-32:4. This profile enables the transmission of 80 bits: 16 bits with full speed, 32 with half speed and 32 with ¼ speed. FIG. 6 shows an example for the division of the digitized signals according to this signal profile. Within a frame the cell sequence of 4 cells resulting from the signal profile repeats every fourth cell since the maximum multiplex rate is 4 give this signal profile. The arrows show that the signal group 1 (S1) is updated with every cell, the signal group 2 (S2) is updated with every second cell and the signal group 3 (S3) is updated with every fourth cell. All three signal groups together form a signal vector with a length of 80 bits.

The access to the signal vector ensues only in the end apparatus and is controlled by the signal access module SAS. The entire signal vector is reconstructed on the basis of the knowledge about the current signal vector and the FPI of each cell. In the transmission direction, under consideration of the current signal profile the signal vector is correspondingly deconstructed into the segments with 40 bits each and dispatched.

Figure 7:
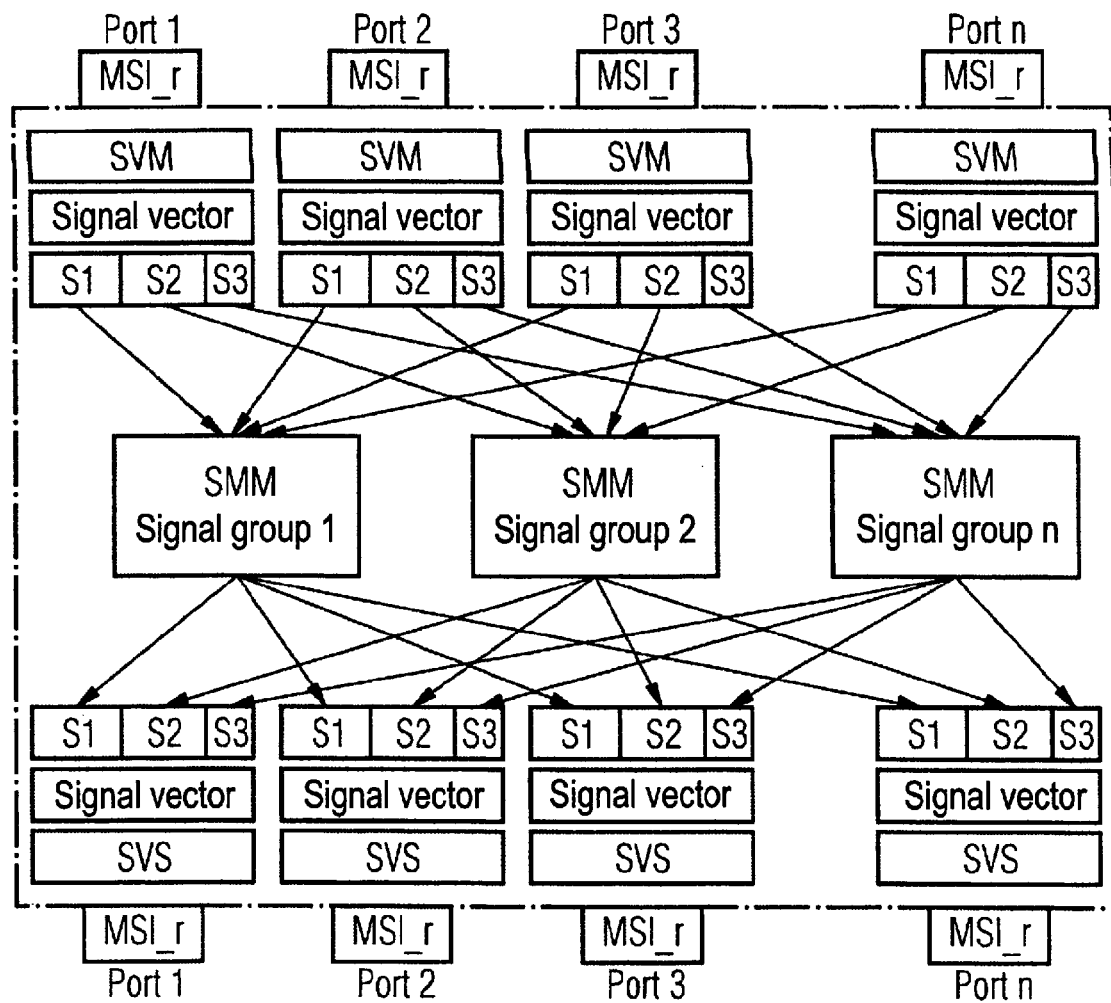
FIG. 7 shows an example for the multiplexing of the signals in a switching station.

In a switching station the received signals for all ports are multiplexed in the output signals for all ports. In the present example the multiplexing ensues to reduce the logical cost only within the respective signal group. This prevents that a signal received in signal group 1 can be sent in signal group 2. FIG. 7 exemplarily shows the multiplexing of the signals in a signal multiplexer module SMS of a switching station. The SMS generates the entire signal vector for the transmission and reception direction for each port. The signal vector is composed from the received cells via the signal vector generator SVM (Signal Vector Merger). In the transmission direction the splitting of the signal vector into the 40-bit segments for each cell ensues via the signal vector splitter SVS (Signal Vector Splitter). A signal multiplexer matrix SMM that generates the transmission signal bits of a signal group for each port as a function of all input signal bits for this same signal group is associated with each signal group.

Figure 8:
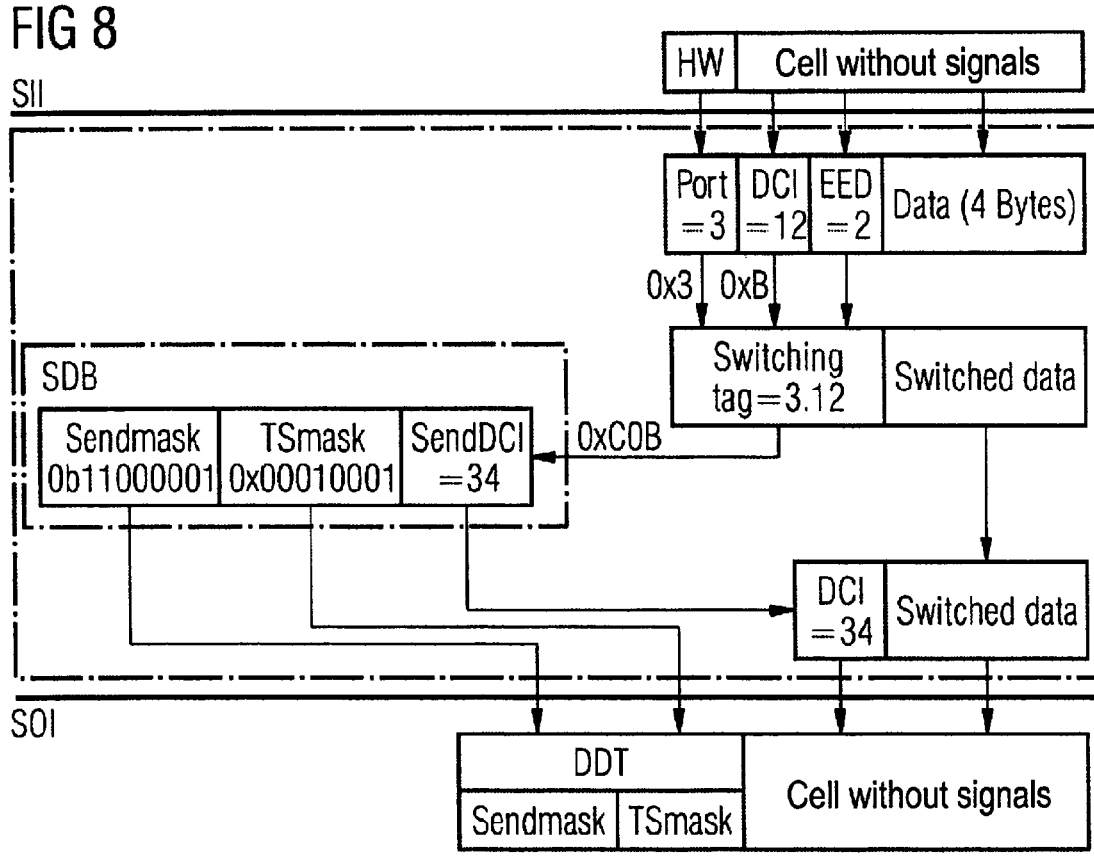
FIG. 8 shows an example for the data switching in a switching station.

The transmission of the data is implemented in a switching station on the basis of the connection information DCI of the cell. This ensues via the data switching module DXS. FIG. 8 shows an example for the data switching within a switching station. The DCI of a received cell identifies the connection and the physical number of the port. In this regard FIG. 8 shows the data flow from a received cell to a sent cell. The received cell is received via the switch input interface (SII: Switch Input Interface). The signals of the cell were previously extracted in the cell processing module CCS. In addition to the information in the cell, the information about the reception port is supplied by the hardware of the switching station. As a first processing step a switch identifier is formed from the port information and the DCI. The switch identifier is used as address information for the switching databank (SDB: Switching DataBase). In the above example the DCI of 11 is encoded as b0000001011 and the port 3 is encoded as 0b11. This leads to a switch identifier of 0b110000001011 (=0xC0B). The associated memory location in the switching station contains the following information:

SendDCI is identical to the DCI of the outgoing cell. The translation of the DCI within the switching station enables a high flexibility in system design since the DCI does not have to be unique within the entire network.

TSmask specifies the time slice or the time slices within the frame that are allowed the transmission of this cell. The association of the time slices ensures a high QoS. In the present example a frame comprises 8 time slices. In the above example the value of 0x00010001 means that the time slices 0 and 4 can be used for the transport of the cell. The time slice of a cell is encoded as an FPI in the header of the cell.

SendMask defines at which ports the cell must be send. The present system enables point-to-point connections with one target port or point-to-multipoint connections with more than one target port. The value of 0x11000001 in the above example indicates that the cell must be sent to the ports 0, 6 and 7 of the switching station. All entries into the switching databank SDB ensue through the administration software via the administration port.

SiDaNet supports both cells with QoS and cells without QoS. The QoS is realized in that one or more of the in total 1024 time slices provided by a sub-frame are associated with a connection. The network is preferentially reserved for the corresponding connection during this time slice or these time slices. For connections for which no QoS is required, the remaining time slices can be used without fixed association. Additional time slices can be used that are reserved for fixed connections but are currently not occupied with a cell. However, no fixed transfer time can be guaranteed for these connections.

For the transmission of the signals, a static multiplex scheme for the individual signal bits is ensured via the respective configuration of the network components. The place of every single signal bit in the cells is ensured via this configuration of the signal multiplexer measurement devices, such that it cannot occur that two or more signal bits are available to occupy one position in the outgoing cell. The QoS is thus ensured for the signals in every case. The bandwidth for the transfer of the data is controlled by the data access module (DAS) in the terminal equipment. This module comprises a sub-frame counter that establishes precisely one of the 1024 possible time slices in connection with the current FPI. An information unit (TMT: Tag Memory Transmit) contained in the data access module comprises the information about which connection is associated with this established time slice. The switching station has no information whatsoever about the sub-frames, only about the position of the respective cell within the individual frame. This information is encoded within the FPI, which is part of the header of the cell. The switch databank SDB in the switching station comprises only the association of the incoming connection with the outgoing connections, the outgoing ports and the position of the cell within the frame.

Figure 9:
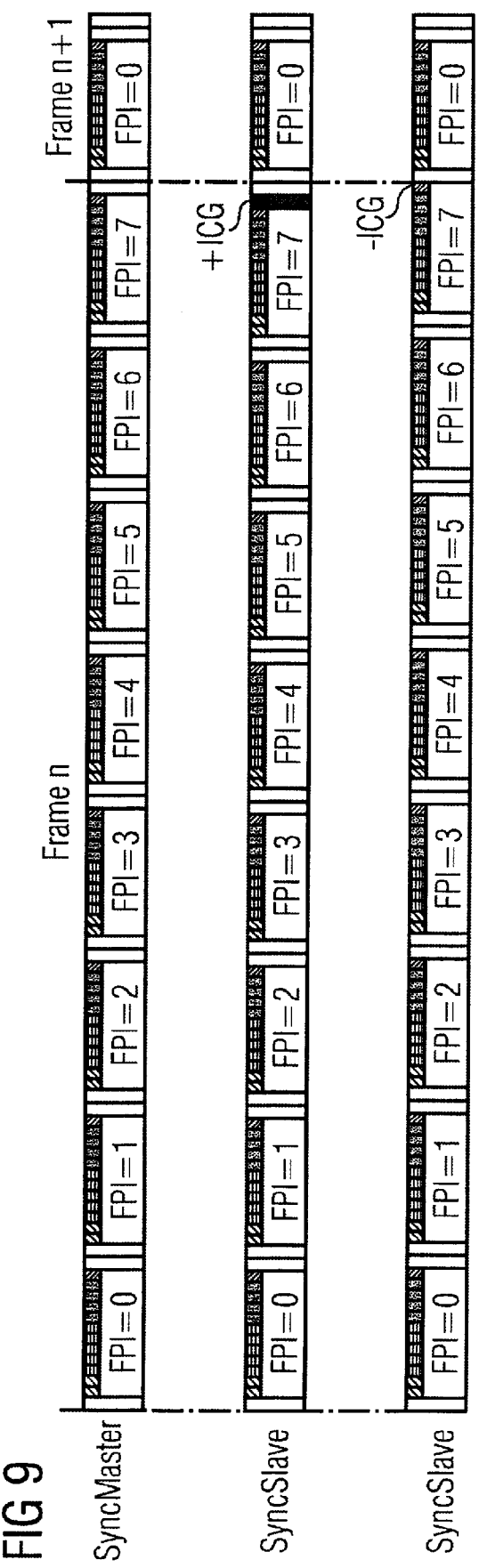
FIG. 9 shows an example for the adaptation of the length of the fill characters between the cells of a frame for synchronization.

To ensure a fixed, determined and calculable delay time of the transmission, a high synchronization of the network components is required. Easily differentiated transmission frequencies of the individual network components (which trace back to the limited precision of the local quartz oscillators used for the timing in the components) are compensated with a variable frame length. This ensues via an adaptation of the fill characters (ICG) between the cells of a frame. FIG. 9 shows this adaptation to an example in which is respectively shown one frame with 8 successive cells and the fill characters situated between them. The uppermost frame that is sent by the sync master comprises fill characters of constant length with respectively two symbols, i.e. two bytes. Shown below this is the frame of a sync slave whose local oscillator frequency is too high relative to that of the sync master. In this case the transfer of the 8 cells by the sync slave has already ended before the eighth cell was received. In order to bridge this time difference, a third ICG byte is added at the end of the frame. In the reverse case of a clock that is too slow frequency relative to the sync slave, the eighth cell was already received, but the transmission procedure still proceeds. To shorten the time for the transmission of the first cell of the next frame (n+1), in this case an ICG byte is omitted as this is shown in the lower portion of the Figure. The last symbol of the fill characters can respectively represent a sync symbol.

The adaptation of the frame length via addition or omission of an ICG symbol is implemented in a device synchronization module DSS or in a switch synchronization module SSS. Since the differences in the transmission frequencies due to the limited precision of the local oscillators are only slight, a correction ensues only in a few frames, for example in perhaps every hundredth frame.

The synchronization of the network components ensues via the sync master, which generates a global transmission point in time (MTM: Master Transmit Moment) and thus the global clock reference at constant time intervals tcell. The switching stations (which are configured as sync repeaters) and the terminal equipment synchronize with this global start point in time. This ensues via the receipt of cells of the sync master. The underlying transmission point in time a the sync master can be calculated in reverse from the reception point in time of each cell at a component. The corresponding transmission times between the individual network components are known and constant. The cells sent from these components are thus synchronized so that the subsequently switching stations or terminal equipment can also be synchronized to the global transmission points in time on the basis of the respectively known transmission time stored in the respective terminal equipment unit or the respective switching station. The synchronization thereby ensues via the respective synchronization modules DSS or, respectively, SSS. In the present example synchronization hereby occurs not at every single cell but rather only at the first cell of each frame. With the time clock of the local oscillator of the component, the further global transmission points in time within a frame can be calculated based on the time intervals (tcell) between the global transmission points in time, which time intervals (tcell) are known in the system. An adaptation given the slight deviations (already mentioned further above) then ensues via the length of the fill characters between the cells. In every case it is ensured with this synchronization that the first cell of each frame is respectively sent precisely at a global transmission point in time.

In addition to this synchronization of the global transmission points in time MTM (and, associated therewith, of the time slices), a synchronization of the sub-frame counter in the individual terminal equipment also ensues. In the present example this is realized in that the sync master dispatches a synchronization cell in every 1024th time slice, which synchronization cell exhibits an FPI of 0. This cell is received at the terminal equipment and used for the synchronization of its sub-frame counter.

In the present example the interval $t_{cell}$ between two successive global transmission points in time MTM must be sufficiently large in order to be able to transfer the complete cell with 12 bytes and the additional 2 bytes of the ICG via the fastest link of the entire network. The transmission speed of the fastest link of the network thus predetermines the timing of the network. In the present example a cell length $t_{cell}$ of 112 ns is selected given a link of 1 Gbit/s. Each cell contains 12 bytes, or 96 bits. Each cell is transferred with the ICQ of 2 bytes. Thus 112 bits are transferred in total with each cell. With a bit length of 1 ns, a cell can be transferred every 112 ns. The interval of the global start points in time is thus set to 112 ns.

A further important requirement for the compliance with the QoS is that the transmission times between the individual components are precisely known and are taken into account in the synchronization. These are the transfer times on the transmission path between the components and the internal processing times in the components. These can be precisely measured before the start-up of the network.

Although modifications and changes may be suggested by those skilled in the art, it is the invention of the inventors to embody within the patent warranted heron all changes and modifications as reasonably and properly come within the scope of their contribution to the art.

We claim as our invention:

1. A method for data and signal transmission between terminal equipment via at least one switching station in a distributed system, comprising the steps of:

combining data to be transmitted and digital signals to be transmitted into respective cells that each contain at least one block for the digitized signals, at least one block for the data, and a header;

in said header, incorporating connection information designating at least one transfer target or relay target for said data;

synchronizing said terminal equipment and said at least one switching station; and synchronously transferring said cells between said terminal equipment via said at least one switching station according to said connection information.

2. A method as claimed in claim 1 comprising incorporating said digitized signals into the respective cells independently of said connection information.

3. A method as claimed in claim 1 comprising:

in a freely configurable register in each switching station, storing at least one specified relay target for the digital signals in the respective cells;

upon receipt of each cell at each switching station, reading out the header and at least the digitized signals thereof; and at that switching station, generating and transmitting a new cell corresponding to the connection information in the header of the readout cell and said specified relay target for the digitized signals of the readout cell.

4. A method as claimed in claim 1 comprising combining the respective cells into periodically recurring frames and transferring said cells in said frames; and Incorporating information describing a position of each cell within a frame into the header of that cell.

5. A method as claimed in claim 4 comprising inserting fill characters between respective cells within the frame.

6. A method as claimed in claim 5 comprising adapting a length of the inserted fill characters to precisely synchronize transfer of said cells.

7. A method as claimed in claim 4 wherein said digital signals are comprised of bits, and comprising distributing bits of at least one of said digital signals among a plurality of cells within a frame.

8. A method as claimed in claim 4 comprising including, in at least some of said frames, a periodically recurring subframe comprised of a fixed number of time slices, and reserving at least one of said time slices for transfer of connections for data and signal transmission between terminal equipment for which a quality of service is required.

9. A method as claimed in claim 1 comprising incorporating an error code into each cell dependent on the content of that cell, and in the at least one switching station or at least one terminal equipment, identifying receipt of incorrect cells from said error code.

10. A method as claimed in claim 9 comprising, upon detection of an incorrect cell, discarding values of the digital signals therein.

11. A method as claimed in claim 1 comprising synchronizing operation of said terminal equipment to cause the respective cells to arrive at said at least one switching station at a point in time allowing the received cells to be distributed immediately without a time delay.

12. A network for data and signal transmission comprising:

a plurality of network components including at least two terminal equipment units and at least one switching station in communication with each of said at least two terminal equipment units;

each of said network components comprising a transmission module that transmits respective cells, comprising data and digital signals and a header to another of said network components, said header containing connection information designating at least one transmission target or relay target for the data in that cell;

each network component further comprising a synchronization module that synchronizes that network component with other network components dependent on points in time of reception of the respective cells and known transmission and processing times; and each transmission module synchronously transferring said cells via said at least one switching station according to said connection information.

13. A network as claimed in claim 12 wherein each of said switching station comprises a freely configurable register in which at least one specified relay goal for the digital signals in the respective cells is stored, and at least one cell processing module, a data switching module, and a signal multiplexer module, said cell processing module reading out the header of each received cell at the switching station and reading out at least the digital signals of that cell, and generating a new cell corresponding to the connection information in the readout header and the specified relay target for that cell stored in the register.

14. A network as claimed in claim 13 wherein the transmission modules in the respective switching stations transmit respective cells combined into periodically recurring frames, and insert fill characters between the respective cells within each frame.

15. A network as claimed in claim 14 wherein said synchronization modules in each switching station insert said fill characters with a length adapted for precise synchronization in transmission of the respective cells.

* * * * *